(12) United States Patent
Zhou et al.

(10) Patent No.: US 12,098,373 B2
(45) Date of Patent: *Sep. 24, 2024

(54) BACILLUS SUBTILIS EFFICIENTLY-INDUCED EXPRESSION SYSTEM BASED ON ARTIFICIAL SERIES PROMOTER

(71) Applicant: Jiangnan University, Wuxi (CN)

(72) Inventors: Zhemin Zhou, Wuxi (CN); Wenjing Cui, Wuxi (CN); Laichuang Han, Wuxi (CN); Wenliang Hao, Wuxi (CN); Li Zhou, Wuxi (CN); Zhongmei Liu, Wuxi (CN); Yu Yan, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 803 days.

This patent is subject to a terminal disclaimer.

(21) Appl. No.: 17/160,582

(22) Filed: Jan. 28, 2021

(65) Prior Publication Data

US 2021/0163963 A1 Jun. 3, 2021

Related U.S. Application Data

(63) Continuation of application No. PCT/CN2019/078809, filed on Mar. 20, 2019.

(30) Foreign Application Priority Data

Dec. 17, 2018 (CN) .......................... 201811542046.0

(51) Int. Cl.
*C12N 15/75* (2006.01)

(52) U.S. Cl.
CPC ........ *C12N 15/75* (2013.01); *C12N 2800/101* (2013.01); *C12N 2830/002* (2013.01); *C12N 2830/005* (2013.01); *C12N 2830/006* (2013.01)

(58) Field of Classification Search
CPC .............. C12N 15/75; C12N 2800/101; C12N 2830/002; C12N 2830/005; C12N 2830/006
See application file for complete search history.

(56) References Cited

U.S. PATENT DOCUMENTS 8,512,982 B2 * 8/2013 Cervin .................. C12N 15/63
536/23.7

FOREIGN PATENT DOCUMENTS

CN 104789566 A 7/2015
CN 105779444 A 7/2016
(Continued)

OTHER PUBLICATIONS

Makino, T., Skretas, G. & Georgiou, G. Strain engineering for improved expression of recombinant proteins in bacteria. Microb Cell Fact 10, 32 (2011) (Year: 2011).*
(Continued)

*Primary Examiner* — Nancy J Leith
*Assistant Examiner* — Shabana S Meyering
(74) *Attorney, Agent, or Firm* — IPRO, PLLC (57) ABSTRACT

The present disclosure discloses a *Bacillus subtilis* efficiently-induced expression system based on an artificial series promoter, and belongs to the technical field of gene engineering. According to the present disclosure, an efficient artificial series constitutive promoter is used, and by compositely designing the promoter and elements (a repressor and a binding site thereof) relevant to an operon, the activity of the constitutive promoter is regulated and controlled by an inducer to finally construct the *B. subtilis* efficiently-induced expression system induced by the inducer. The result indicates that compared with a $P_{43}$ strongly constitutive promoter, the activity of the artificial series promoter in the system is about 15 times higher. The activity of the (Continued)

promoter can be accurately controlled by adding different concentrations of inducers. Therefore, the efficient expression system is simple in structure, high in activity and strict in regulating and controlling and has wide application prospects in heterologous protein efficient expression and synthetic biology research.

10 Claims, 4 Drawing Sheets

Specification includes a Sequence Listing.

(56) References Cited

FOREIGN PATENT DOCUMENTS

| | | | |
|---|---|---|---|
| CN | 109486847 A | 3/2019 | |
| EP | 0135045 B1 | 12/1990 | |
| JP | 2009022293 A | * 2/2009 | ......... C12N 15/1051 |

OTHER PUBLICATIONS

Yan et al., J. Agric. Food Chem. 2018, 66, 6, 1444-1451 (Year: 2018).*

Bervoets I, Van Brempt M, Van Nerom K, Van Hove B, Maertens J, De Mey M, Charlier D. A sigma factor toolbox for orthogonal gene expression in *Escherichia coli*. Nucleic Acids Res. Feb. 28, 2018;46(4):2133-2144. doi: 10.1093/nar/gky010. (Year: 2018).*

Zuber, P. and Losick, R. Use of a lacZ fusion to study the role of the spoO genes of Bacillus subtilis in developmental regulation Cell 35 (1), 275-283 (1983). (Year: 1983).*

* cited by examiner

SEQUENCE LISTING

<160> NUMBER OF SEQ ID NOS: 17

<210> SEQ ID NO 1
<211> LENGTH: 245
<212> TYPE: DNA
<213> ORGANISM: Artificial Sequence
<220> FEATURE:
<223> OTHER INFORMATION: Synthetic DNA

<400> SEQUENCE: 1
aagcaaaaaa agtttgactc ggtattttaa ctatgttaat attgtaaaat gccaatgtat      60 atttttataaa aaaattgaaa cctttttgaaa cgaagctcgt atacatacag accggtgaag     120
gtgtaactat atcctatttt ttcaaaaaat atttttaaaaa cgagcaggat ttcagaaaaa     180
atcgtggaat tgatacacta atgcttttat tcgaacatca tatttaaagt acaggaggtc     240
cacat                                                                 245

<210> SEQ ID NO 2
<211> LENGTH: 230
<212> TYPE: DNA
<213> ORGANISM: Artificial Sequence
<220> FEATURE:
<223> OTHER INFORMATION: Synthetic DNA

<400> SEQUENCE: 2
aagcaaaaaa agtttgactc ggtattttaa ctatgttaat attgtaaaat gccaatgtat      60 ttttttattta ccttatgccc gaaatgaaag ctttatgacc taattgtgta actatatcct    120 atttttttcaa aaaatatttt aaaaacgagc aggatttcag aaaaaatcgt ggaattgata    180
cactaatgct tttattcgaa catcatattt aaagtacagg aggtccacat                230

<210> SEQ ID NO 3
<211> LENGTH: 290
<212> TYPE: DNA
<213> ORGANISM: Artificial Sequence
<220> FEATURE:
<223> OTHER INFORMATION: Synthetic DNA

<400> SEQUENCE: 3 atttttataaa aaaattgaaa cctttttgaaa cgaagctcgt atacatacag accggtgaag     60
aagcaaaaaa agtttgactc ggtattttaa ctatgttaat attgtaaaat gccaatgtat     120 ttttttattta ccttatgccc gaaatgaaag ctttatgacc taattgtgta actatatcct    180 atttttttcaa aaaatatttt aaaaacgagc aggatttcag aaaaaatcgt ggaattgata    240
cactaatgct tttattcgaa catcatattt aaagtacagg aggtccacat                290

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
ggaattgtga gcggataaca attcc                                            25

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

```
<400> SEQUENCE: 5
agttagttta ttggataaac aaactaact                              29

<210> SEQ ID NO 6
<211> LENGTH: 42
<212> TYPE: DNA
<213> ORGANISM: Artificial Sequence
<220> FEATURE:
<223> OTHER INFORMATION: Synthetic DNA

<400> SEQUENCE: 6
ctaacggaaa agggattttt gagtgatctt ctcaaaaaat ac               42

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA

<400> SEQUENCE: 7
cctcgtatgt ttcaaagagt gcaccatatg cgg                         33

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
catatggtgc actctttgaa acatacgagg ctaatatcgg                  40

<210> SEQ ID NO 9
<211> LENGTH: 37
<212> TYPE: DNA
<213> ORGANISM: Artificial Sequence
<220> FEATURE:
<223> OTHER INFORMATION: Synthetic DNA

<400> SEQUENCE: 9
aagatcactc aaaaatccct tttccgttag cttttc                      37

<210> SEQ ID NO 10
<211> LENGTH: 54
<212> TYPE: DNA
<213> ORGANISM: Artificial Sequence
<220> FEATURE:
<223> OTHER INFORMATION: Synthetic DNA

<400> SEQUENCE: 10
ggaattgtga gcggataaca attccatgct tttattcgaa catcatattt aaag  54

<210> SEQ ID NO 11
<211> LENGTH: 51
<212> TYPE: DNA
<213> ORGANISM: Artificial Sequence
<220> FEATURE:
<223> OTHER INFORMATION: Synthetic DNA

<400> SEQUENCE: 11
ggaattgtta tccgctcaca attcctagtg tatcaattcc acgattttt c      51

<210> SEQ ID NO 12
```

```
<211> LENGTH: 58
<212> TYPE: DNA
<213> ORGANISM: Artificial Sequence
<220> FEATURE:
<223> OTHER INFORMATION: Synthetic DNA

<400> SEQUENCE: 12
agttagttta ttggataaac aaactaacta tgcttttatt cgaacatcat atttaaag        58

<210> SEQ ID NO 13
<211> LENGTH: 55
<212> TYPE: DNA
<213> ORGANISM: Artificial Sequence
<220> FEATURE:
<223> OTHER INFORMATION: Synthetic DNA

<400> SEQUENCE: 13
agttagtttg tttatccaat aaactaactt agtgtatcaa ttccacgatt ttttc        55

<210> SEQ ID NO 14
<211> LENGTH: 44
<212> TYPE: DNA
<213> ORGANISM: Artificial Sequence
<220> FEATURE:
<223> OTHER INFORMATION: Synthetic DNA

<400> SEQUENCE: 14
ttaattgcgt tgcgcctaac ttataggggt aacacttaaa aaag        44

<210> SEQ ID NO 15
<211> LENGTH: 40
<212> TYPE: DNA
<213> ORGANISM: Artificial Sequence
<220> FEATURE:
<223> OTHER INFORMATION: Synthetic DNA

<400> SEQUENCE: 15
agggagacga ttttgatggt tattattcaa attgcagatc        40

<210> SEQ ID NO 16
<211> LENGTH: 32
<212> TYPE: DNA
<213> ORGANISM: Artificial Sequence
<220> FEATURE:
<223> OTHER INFORMATION: Synthetic DNA

<400> SEQUENCE: 16
ttgaataata accatcaaaa tcgtctccct cc        32

<210> SEQ ID NO 17
<211> LENGTH: 32
<212> TYPE: DNA
<213> ORGANISM: Artificial Sequence
<220> FEATURE:
<223> OTHER INFORMATION: Synthetic DNA

<400> SEQUENCE: 17
acccctataa gttaggcgca acgcaattaa tg        32
```

BACILLUS SUBTILIS EFFICIENTLY-INDUCED EXPRESSION SYSTEM BASED ON ARTIFICIAL SERIES PROMOTER

REFERENCE TO SEQUENCE LISTING

The instant application contains a Sequence Listing in ASCII plain text file format as a file named "Seq.txt", created on Jan. 26, 2021, of 4368 bytes in size, and which is hereby incorporated by reference in its entirety.

TECHNICAL FIELD

The present disclosure relates to a *Bacillus subtilis* efficiently-induced expression system based on an artificial series promoter, and belongs to the technical field of gene engineering.

BACKGROUND

*B. subtilis* is a gram positive type strain which is widely applied to exogenous protein expression, and it is widely applied to the aspect of industrial enzyme preparation production because of the ability to efficiently express exogenous proteins. Promoters are the most basic elements for constructing an efficient expression system, and the activity of the promoters directly determines the efficiency of the expression system. Functionally, the promoters are mainly divided into constitutive promoters and inducible promoters. The constitutive promoters can express exogenous genes at all growth stages of bacteria, while the inducible promoters show inactivity or low activity when they are not induced, and after an inducer is added, the activity of the promoters is greatly improved, so that the exogenous genes are efficiently expressed. The inducible promoters are widely applied because of their controllable activity, and people can control the expression time and intensity of the exogenous genes by regulating and controlling a reagent and the concentration of the added inducer. At present, what are widely applied to the *B. subtilis* are mainly an IPTG inducible system and a xylose inducible system, wherein the IPTG inducible system is mainly constructed based on a pHT series vector, using non-natural hybrid promoters and Lac repressors and binding sites of *Escherichia coli*. The xylose inducible system usually uses natural PxyIA promoters and XylR repressors.

Although IPTG, xylose and other inducible systems have been widely used, the low expression of the exogenous proteins has always been a key problem restricting system application due to limited promoter activity. People usually adopt two strategies of modifying natural promoters and redesigning artificial promoters to improve the activity and stability of the promoters. However, the high-activity promoters are often unable to be used in the construction of an efficiently-induced exogenous gene expression system, mainly because the promoters and other elements of a gene expression regulating and controlling system are often incompatible, and the activity of the high-activity promoters are often unable to be effectively suppressed by the repressors. Therefore, how to construct the strictly regulated and controlled induced exogenous gene expression system based on the efficient promoters is a hot topic in the development of novel expression systems at present.

SUMMARY

The present disclosure provides an element for regulating and controlling gene expression, including: (1) a vector, (2) an artificial series promoter, (3) a gene for coding a repressor, and (4) a DNA fragment located at downstream of a transcriptional start site of the promoter and capable of being bound to the repressor, and the artificial series promoter includes $P_{AWH-D30-106}$, $P_{AH-D75-106}$ or $P_{WAH-D75-106}$, wherein a nucleotide sequence of $P_{AWH-D30-106}$ is shown as SEQ ID NO:1, a nucleotide sequence of $P_{AH-D75-106}$ is shown as SEQ ID NO:2, and a nucleotide sequence of $P_{WAH-D75-106}$ is shown as SEQ ID NO:3.

In one implementation of the present disclosure, the repressor is LacI, XylR, AraC or TetR.

In one implementation of the present disclosure, when the repressor is LacI, expression of a target gene is induced by IPTG.

In one implementation of the present disclosure, when the repressor is XylR, expression of a target gene is induced by xylose.

In one implementation of the present disclosure, when the repressor is AraC, expression of a target gene is induced by arabinose.

In one implementation of the present disclosure, when the repressor is TetR, expression of a target gene is induced by tetracycline.

In one implementation of the present disclosure, the vector is pHT-01.

In one implementation of the present disclosure, a host for expressing the target gene is *B. subtilis*.

In one implementation of the present disclosure, a host for expressing the target gene includes, but is not limited to, *B. subtilis* 168, *B. subtilis* W1B400, *B. subtilis* WB600 or *B. subtilis* WB800.

In one implementation of the present disclosure, the target gene includes an exogenous gene or an endogenous gene.

In one implementation of the present disclosure, the target gene includes an enzyme gene or a non-enzyme gene.

The present disclosure further provides a recombinant plasmid, expressing any foregoing element for regulating gene expression.

The present disclosure further provides a genetic engineering bacterium, expressing the recombinant plasmid.

The present disclosure further provides a method for regulating and controlling target gene expression, wherein the above element for regulating gene expression regulates and controls expression of a target gene.

The present disclosure further provides application of the above element for regulating and controlling gene expression to preparation of a target protein.

The present disclosure further provides application of the above element for regulating and controlling gene expression to a field of food, chemical engineering or pharmaceuticals.

The present disclosure further provides application of the above genetic engineering bacterium to preparation of a target protein.

The present disclosure further provides application of the above genetic engineering bacterium to a field of food, chemical engineering or pharmaceuticals.

According to the present disclosure, an efficient artificial series constitutive promoter is used, and by compositely designing the promoter and elements (a repressor and a binding site thereof) relevant to an operon, the activity of the constitutive promoter is regulated and controlled by an inducer to finally construct a *B. subtilis* efficiently-induced expression system induced by the inducer. The result indicates that compared with a $P_{43}$ strongly constitutive promoter, the activity of the artificial series promoter in the system is about 15 times higher. The activity of the promoter can be accurately controlled by adding different concentrations of inducers. Therefore, the efficient expression system is simple in structure, high in activity and strict in regulating and controlling and has wide application prospects in heterologous protein efficient expression and synthetic biology research.

DETAILED DESCRIPTION

1. A construction method of a plasmid: A primer including a promoter sequence is designed, and PrimeSTAR MAX DNA polymerase (purchased from Takara with an article number of R045Q) is used for full plasmid PCR by taking a pHT01 plasmid as a skeleton template. PCR procedures are: pre-denaturation at 98° C. for 1 min, circulation including denaturation at 98° C. for 30 s, annealing at 50° C. for 30 s, and extending at 72° C. for 1 min for a total of 30 times, and final extending at 72° C. for 10 min. Then, the plasmid template is digested and removed with a restriction enzyme DpnI to purify a PCR product. Fragments needing to be cloned are amplified through the same method. Then, the plurality of fragments are assembled through an Infusion reassembling method to be transformed into E. coli JM109 competent cells.

2. A detection method of an sfGFP fluorescence intensity: A to-be-detected sample is centrifuged at 12000×g for 2 min, and bacteria are collected, washed with PBS 3 times, and then diluted with PBS to a certain concentration to obtain a bacterium suspension. 200 μL of the bacterium suspension is taken to a 96-well ELISA plate, and the 96-well ELISA plate is placed into a fluorescence microplate reader for fluorescence detection. Fluorescence is detected with excitation light of 485 nm and absorbed light of 528 nm.

3. A medium: LB medium ($L^{-1}$): 10 g of tryptone, 10 g of NaCl, 5 g of a yeast extract, pH 7.0, and 20 g of agar powder added when a solid medium is prepared.

4. A transformation method of B. subtilis 168: Single-colony B. subtilis 168 is picked to be inoculated into a 2 mL SPI medium and subjected to shaking culture at 37° C. for 12 h-14 h. 100 μL of a culture is taken to be inoculated into a 5 mL SPI medium and subjected to shaking culture at 37° C. for 4-5 h till $OD_{600}$ is about 1.0, and at this time, 200 μL of a bacterium solution is pipetted to be transferred into a 2 mL SPII medium and subjected to shaking incubation at 37° C. and 100 r·min$^{-1}$ for 1.5 h. 20 μL of a 100×EGTA (ethylene glycol-bis(α-aminoethyl ether)-N,N,N',N'-tetraacetic acid) solution is added into a tube to be cultured in a shaking table at 37° C. and 100 r·min$^{-1}$ for 10 min, and then each centrifuge tube of 1.5 mL is filled with 500 μL of a mixture. A proper quantity of plasmids verified to be correct by sequencing are added into the tubes, and subjected to blowing-suction uniform mixing to be placed into the shaking table at 37° C. and 100 r·min$^{-1}$ for 2 h. Culture is completed, and about 200 μL of a bacterium solution is sucked to be uniformly smeared on a corresponding selective plate to be cultured at 37° C. for 12 h-14 h.

5. SDS-PAGE detection: 200 μL of a bacterium solution is taken to be centrifuged at 12000×g for 2 min, and bacteria are collected. The bacteria are resuspended with 200 μL of a 20 mM Tris-HCl (pH8.0) buffer solution containing lysozyme at a concentration of 20 μg/mL, and incubated at 37° C. for 30 min to lyse cell walls. Then, 50 μL of 10×Loading Buffer is added, cooked with boiling water for 10 min and then centrifuged at 12000×g for 5 min. 30 μL of a supernatant sample is taken for electrophoresis detection, dyed with Coomassie brilliant blue R250 and destained with a destaining solution, and then an electrophoresis result is analyzed.

Figure 1:
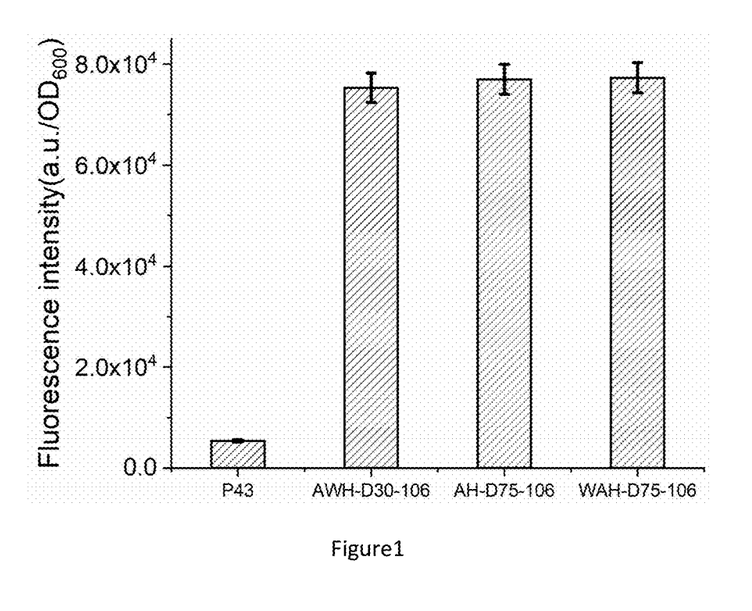
FIG. 1: activity comparison of $P_{AWH-D30-106}$, $P_{AH-D75-106}$ and $P_{WAH-D75-106}$ with a $P_{43}$ promoter.

Example 1: Activity Identification of Artificial Series Promoters $P_{AWH-D30-106}$, $P_{AH-D75-106}$ and $P_{WAH-D75-106}$ promoters are all artificially constructed core area series hybrid promoters.
Sequences of the $P_{AWH-D30-106}$, $P_{AH-D75-106}$ and $P_{AH-D75-106}$ promoters are respectively shown as SEQ ID NO:1, SEQ ID NO:2 and SEQ ID NO:3.
The promoter $P_{AWH-D30-106}$ shown as SEQ ID NO:1 is cloned onto a pHT01 vector through primers in Table 1 with an sfGFP (Genbank ID: AVR55189.1) expression cassette to substitute a $P_{spac}$ promoter sequence on an original vector. The expression vector is transformed into B. subtilis 168, recombinant bacteria are cultured for 20 h, and the expression level of sfGFP is detected.
In the same way, the promoter $P_{AH-D75-106}$ shown as SEQ ID NO:2 and the promoter $P_{WAH-D75-106}$ shown as SEQ ID NO:3 are respectively adopted to be cloned onto the pHT01 vector with the sfGFP expression cassette to substitute $P_{spac}$ promoter sequences on the original vector. The vector is transformed into the B. subtilis 168 through the same method, recombinant bacteria are cultured for 24 h, and the expression level of sfGFP of recombinant bacterium culture solutions of recombinant plasmids containing $P_{AH-D75-106}$ and $P_{WAH-D75-106}$ is detected.
By comparing with the situation that a common strongly constitutive promoter $P_{43}$ expresses sfGFP, the result shows that the expression levels of the $P_{AWH-D30-106}$, $P_{AH-D75-106}$ and $P_{WAH-D75-106}$ promoters for sfGFP are much higher than the expression level of the $P_{43}$ promoter, and reach about 14 times the expression level of $P_{43}$ (FIG. 1 and Table 2). It shows that the $P_{AWH-D30-106}$, $P_{AH-D75-106}$ and $P_{WAH-D75-106}$ promoters are strongly constitutive promoters with very high activity.

TABLE 1

Primers for constructing expression vector

| Primer | Sequence (5'-3')[a] | Sequence table number |
|---|---|---|
| PpHT-AWH-i1 | CTAACGGAAAAGGGATTTTTGAGTGATCTTCTCA AAAAATAC | SEQ ID NO: 6 |

TABLE 1-continued

Primers for constructing expression vector

| Primer | Sequence (5'-3')[a] | Sequence table number |
|---|---|---|
| PpHT-AWH-i2 | CCTCGTATGTTTCAAAGAGTGCACCATATGCGG | SEQ ID NO: 7 |
| PpHT-AWH-v1 | CATATGGTGCACTCTTTGAAACATACGAGGCTAATATCGG | SEQ ID NO: 8 |
| PpHT-AWH-v2 | AAGATCACTCAAAAATCCCTTTTCCGTTAGCTTTTTC | SEQ ID NO: 9 |

TABLE 2

Activity of artificial series promoters

| Promoter | Fluorescence intensity (a.u./OD$_{600}$) |
|---|---|
| P$_{43}$ | 473 |
| P$_{AWH-D30-106}$ | 6635 |
| P$_{AH-D75-106}$ | 6782 |
| P$_{WAH-D75-106}$ | 6910 |

Example 2: Construction of an IPTG Induced Expression System

Figure 2A:
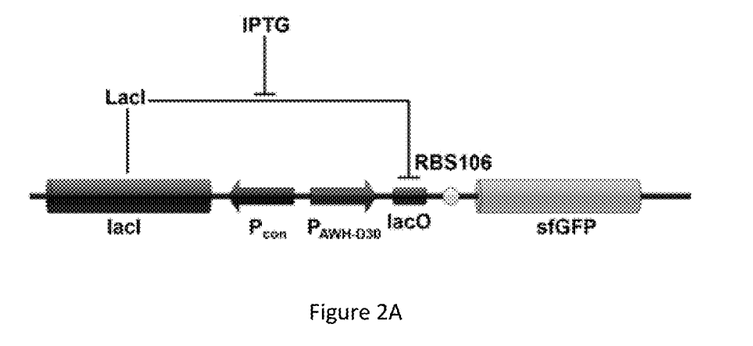
FIG. 2A: IPTG induced system principle.
Figure 2B:
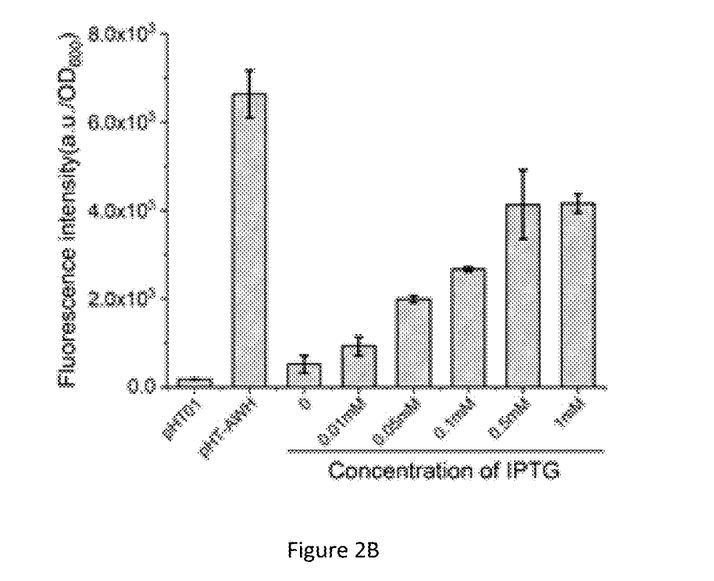
FIG. 2B: IPTG induced system characterization.
Figure 2C:
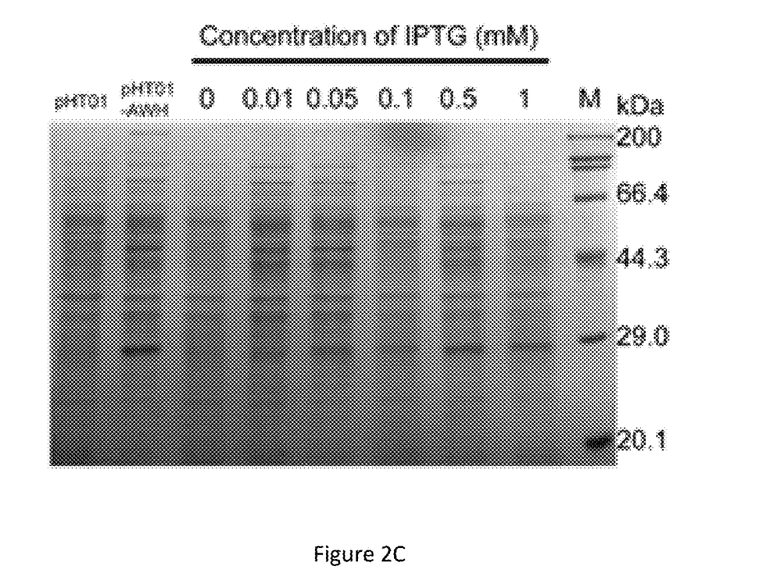
FIG. 2C: verification of sfGFP expression by SDS-PAGE.

A sequence of a binding site of lacI is GGAATTGTGAGCGGATAACAATTCC (SEQ ID NO:4), which is designed on primers P$_{AWH}$-lacO-1 and P$_{AWH}$-lacO-2 in Table 3. The sequence of the Lac protein binding site is cloned to the downstream of a transcriptional start site of a promoter P$_{AWH-D30-106}$ through a full plasmid PCR method. Meanwhile, a repressor protein Lac is expressed through an lacI module on a pHT01 vector skeleton. The IPTG induced expression system (FIG. 2) is constructed.

sfGFP serves as a target protein to characterize the magnitude of an expression quantity to construct a plasmid pHT-AWH-lac-sfGFP. The recombinant plasmid pHT-AWH-lac-sfGFP is transformed into *B. subtilis* 168. Recombinant bacteria are cultured in an LB medium at 37° C. and 200 rpm. After 24 h, the expression level of sfGFP is detected.

In the absence of an IPTG inducer, the repressor protein Lac can be effectively bound to the downstream of a transcriptional start site of a promoter to prevent transcription of downstream genes by RNA polymerase, so that expression of the downstream genes is inhibited. When IPTG is added, the activity of the promoter is released. Within the range of not more than 1 mM, the higher the concentration of the added IPTG is, the stronger the activity of the promoter is. Therefore, expression intensities of the downstream genes with different intensities can be obtained by regulating the usage amount of the IPTG (FIG. 2 and Table 4). SDS-PAGE detection also proves that sfGFP expression with different intensities is obtained through addition of inducers IPTG of different concentrations (FIG. 2).

TABLE 3

Primers for constructing IPTG induced expression vector

| Primer | Sequence (5'-3')[a] | Sequence table number |
|---|---|---|
| PAWH-lacO-1 | GGAATTGTGAGCGGATAACAATTCCATGCTTTTATTCGAACATCATATTTAAAG | SEQ ID NO: 10 |
| PAWH-lacO-2 | GGAATTGTTATCCGCTCACAATTCCTAGTGTATCAATTCCACGATTTTTC | SEQ ID NO: 11 |

TABLE 4

Expression situations of sfGFP induced by IPTG of different concentrations

| Condition | Fluorescence intensity (a.u./OD$_{600}$) |
|---|---|
| pHT-01 | 179 |
| pHT-AWH (uncombined operon) | 6635 |
| 0 mM IPTG | 516 |
| 0.01 mM IPTG | 929 |
| 0.05 mM IPTG | 1993 |
| 0.1 mM IPTG | 2665 |
| 0.5 mM IPTG | 4132 |
| 1 mM IPTG | 4163 |

Example 3: Construction of a Xylose Induced Expression System

A binding site of a repressor protein XylR is cloned to the downstream of a transcriptional start site of a promoter P$_{AWH-D30-106}$ through primers in Table 5. Meanwhile, an lacI gene on a pHT01 vector skeleton is substituted with an xylR gene. An XylR expression module and the xylose induced expression system are constructed. Specific steps are as follows:

The plasmid pHT-AWH-lac-sfGFP constructed in Example 2 is taken as a template, a vector skeleton is amplified through the primer PAWH-xylR-v1/PAWH-xylR-v2 (Table 5), the xylR gene is amplified through the primer PAWH-xylR-i1/PAWH-xylR-i2, two amplified fragments are recombined, and a plasmid with xylR substituting lacI is obtained; then, through the primer PAWH-xylO-1/PAWH-xylO-2, a binding site of lacI is substituted with the binding site AGTTAGTTTATTGGATAAACAAACTAACT (SEQ ID NO:5) of xylR through a full plasmid PCR method; and finally, the plasmid pHT-AWH-xyl-sfGFP is constructed.

The recombinant plasmid is transformed into B. subtilis 168. Recombinant bacteria are cultured in an LB medium at 37° C. and 200 rpm. After 24 h, the expression level of sfGFP is detected.

Figure 3A:
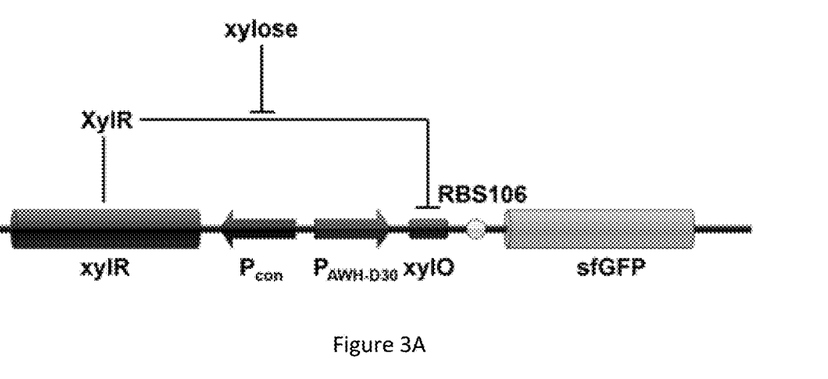
FIG. 3A: xylose induced system principle.
Figure 3B:
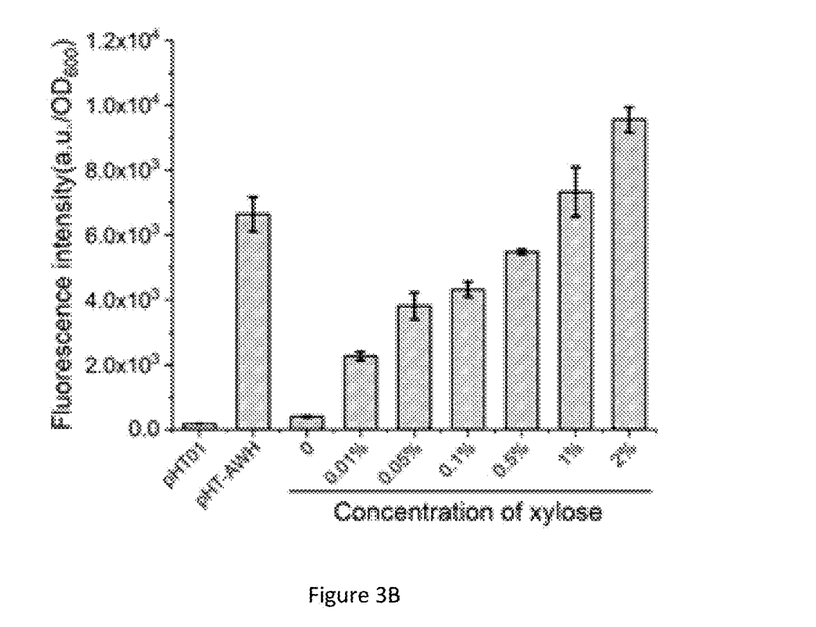
FIG. 3B: xylose induced system characterization.
Figure 3C:
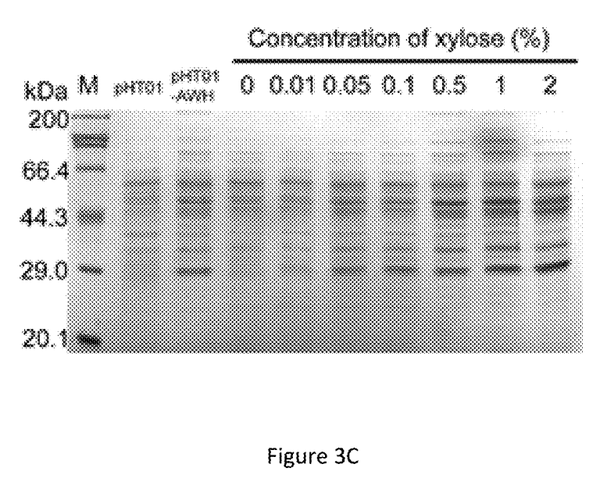
FIG. 3C: verification of sfGFP expression by SDS-PAGE.

In the absence of an inducer xylose, a repressor protein xylR can be effectively bound to the downstream of a transcriptional start site of a promoter to prevent transcription of the promoter by RNA polymerase, so that expression of downstream genes is inhibited (FIG. 3).

When xylose of different concentrations is added, the activity of the promoter is released gradually, and therefore, expression intensities of the downstream genes with different intensities can be obtained by regulating the concentration of xylose. With the gradual increase of the concentration of xylose, a fluorescence signal generated through sfGFP expression is enhanced accordingly. When the concentration of xylose exceeds 1% (W/V), the expression level of sfGFP is even higher than a control pHT-AWH (FIG. 3 and Table 6) of constitutive expression sfGFP. Further, through SDS-PAGE detection, it is proven that sfGFP expression with different intensities is obtained through addition of inducers xylose of different concentrations (FIG. 3).

TABLE 6

Expression situations of sfGFP under different concentrations of xylose

| Condition | Fluorescence intensity (a.u./OD$_{600}$) |
|---|---|
| pHT-01 | 179 |
| pHT-AWH | 6635 |
| (uncombined operon) | |
| 0% xylose | 393 |
| 0.01% xylose | 2263 |
| 0.05% xylose | 3808 |
| 0.1% xylose | 4322 |
| 0.5% xylose | 5480 |
| 1% xylose | 7326 |
| 2% xylose | 9556 |

Example 4: Expression of a Target Gene by a Xylose Induced Expression System

The same strategies as Examples 1-3 are adopted, and the difference is that sfGFP is substituted with other target genes, such as an endogenous gene or an exogenous gene participating in microbial metabolism, to construct a recombinant microorganism containing the xylose induced expression system. The constructed recombinant microorganism is cultured under a suitable condition and induced by inducers xylose of different concentrations. By detecting the gene expression level, it is found that target gene expression results at different intensities can be obtained through addition of the inducers xylose of different concentrations.

Although the present disclosure has been disclosed as above as exemplary examples, it is not intended to limit the present disclosure. Any of those skilled in the art may make various alterations and modifications without departing from the spirit and scope of the present disclosure. Therefore, the protection scope of the present disclosure shall be as defined in the claims.

TABLE 5

Primers for constructing xylose induced expression vector

| Primer | Sequence (5'-3')$^a$ | Sequence table number |
|---|---|---|
| PAWH-xylO-1 | AGTTAGTTTATTGGATAAACAAACTAACTATGCTTT TATTCGAACATCATATTTAAAG | SEQ ID NO: 12 |
| PAWH-xylO-2 | AGTTAGTTTGTTTATCCAATAAACTAACTTAGTGTA TCAATTCCACGATTTTTC | SEQ ID NO: 13 |
| PAWH-xylR-i1 | TTAATTGCGTTGCGCCTAACTTATAGGGGTAACAC TTAAAAAG | SEQ ID NO: 14 |
| PAWH-xylR-i2 | AGGGAGACGATTTTGATGGTTATTATTCAAATTGC AGATC | SEQ ID NO: 15 |
| PAWH-xylR-v1 | TTGAATAATAACCATCAAAATCGTCTCCCTCC | SEQ ID NO: 16 |
| PAWH-xylR-v2 | ACCCCTATAAGTTAGGCGCAACGCAATTAATG | SEQ ID NO: 17 |

What is claimed is:

1. A method, comprising constructing a recombinant plasmid as a regulating and controlling element in an expression host of *Bacillus subtilis* (*B. subtilis*), wherein the recombinant plasmid comprises: (1) a vector, (2) an artificial series promoter, (3) a gene for coding a repressor, and (4) a repressor-binding DNA fragment located at downstream of a transcriptional start site of the artificial series promoter and capable of being bound to the repressor, and the artificial series promoter comprises $P_{AWH\text{-}D30\text{-}106}$, $P_{AH\text{-}D75\text{-}106}$ or $P_{AH\text{-}D75\text{-}106}$ with nucleotide sequences that are set forth as SEQ ID NO:1, SEQ ID NO:2 and SEQ ID NO:3, respectively; wherein the constructing the recombinant plasmid comprises cloning the artificial series promoter, the gene for coding a repressor, and the repressor-binding DNA fragment into the vector that has a target gene of interest, and obtaining the recombinant plasmid; wherein the method further comprises transforming the recombinant plasmid into a culture of *B. subtilis*, growing the culture under a predetermined condition to obtain recombinant clones and inducing expression of the target gene and producing a target protein by growing the recombinant clones under a predetermined inducing condition, wherein adding different amounts of an inducer result in different levels of induced expression of the target gene.

2. The method according to claim 1, wherein the repressor is LacI, XylR, AraC or TetR.

3. The method according to claim 2, wherein when the repressor is LacI, the growing the recombinant clones under a predetermined inducing condition further comprises adding IPTG as the inducer and inducing the expression of the target gene.

4. The method according to claim 2, wherein when the repressor is XylR, and the growing the recombinant clones under a predetermined inducing condition further comprises adding xylose and inducing the expression of the target gene by xylose.

5. The method according to claim 2, wherein when the repressor is AraC, the growing the recombinant clones under a predetermined inducing condition further comprises adding arabinose as the inducer and inducing the expression of the target gene by arabinose.

6. The method according to claim 2, wherein when the repressor is TetR, the growing the recombinant clones under a predetermined inducing condition further comprises adding tetracycline as the inducer and inducing the expression of the target gene by tetracycline.

7. The method according to claim 1, wherein the vector is pHT-01.

8. The method according to claim 1, wherein the *B. subtilis* is *B. subtilis* 168, *B. subtilis* W1B400, *B. subtilis* WB600 or *B. subtilis* W1B800.

9. A recombinant DNA plasmid for regulating and controlling gene expression, comprising: (1) a vector, (2) an artificial series promoter, (3) a gene for coding a repressor, and (4) a DNA fragment located at downstream of a transcriptional start site of the promoter and capable of being bound to the repressor, wherein the artificial series promoter comprises $P_{AWH-D30-106}$, $P_{AH-D75-106}$ or $P_{AH-D75-106}$ with nucleotide sequences that are set forth as SEQ ID NO:1, SEQ ID NO:2 and SEQ ID NO:3, respectively; wherein an expression host is *Bacillus subtilis* (*B. subtilis*).

10. The recombinant DNA plasmid of claim 9, wherein the vector comprises a target gene that is capable of expressing a target protein.

* * * * *